United States Patent
Leahy et al.

(10) Patent No.: US 10,512,395 B2
(45) Date of Patent: Dec. 24, 2019

(54) MONTAGING OF WIDE-FIELD FUNDUS IMAGES

(71) Applicant: Carl Zeiss Meditec, Inc., Dublin, CA (US)

(72) Inventors: Conor Leahy, Dublin, CA (US); Keith E. O'Hara, Pleasanton, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 300 days.

(21) Appl. No.: 15/582,212

(22) Filed: Apr. 28, 2017

(65) Prior Publication Data

US 2017/0316565 A1    Nov. 2, 2017

Related U.S. Application Data

(60) Provisional application No. 62/329,372, filed on Apr. 29, 2016.

(51) Int. Cl.
*G06T 3/00* (2006.01)
*H04N 5/232* (2006.01)
(Continued)

(52) U.S. Cl.
CPC .......... *A61B 3/0041* (2013.01); *A61B 3/0025* (2013.01); *A61B 3/102* (2013.01);
(Continued)

(58) Field of Classification Search
CPC ..... G06T 3/4038; G06T 3/0093; G06T 5/006; G06T 2207/30041; G06T 3/0068; H04N 5/23238
See application file for complete search history.

(56) References Cited

U.S. PATENT DOCUMENTS

| 5,680,150 A | 10/1997 | Shimizu et al. |
| 5,943,116 A | 8/1999 | Zeimer |

(Continued)

FOREIGN PATENT DOCUMENTS

| WO | 2015/100294 A1 | 7/2015 |
| WO | 2016/040935 A1 | 3/2016 |

OTHER PUBLICATIONS

Brown et al., "Automatic Panoramic Image Stitching using Invariant Features", International Journal of Computer Vision, vol. 74, No. 1, 2007, pp. 59-73.

(Continued)

*Primary Examiner* — Andrew M Moyer
*Assistant Examiner* — Dennis Rosario
(74) *Attorney, Agent, or Firm* — Morrison & Foerster LLP

(57) ABSTRACT

Methods to create montages of wide-field fundus images, while correcting for the projective distortion inherent to an imaging system are described. The methods use specific knowledge of the imaging geometry of the particular imaging system to map the fundus images onto a set of 3D ray vectors, which allows them to be stitched together efficiently and precisely. After co-aligning the images using feature detection and matching, the registered images are projected back into 2D to generate the final montaged image. The method could be used on any type of wide-field fundus images including, but not limited to, those generated from optical coherence tomography, optical coherence tomography angiography, and broad-line fundus imaging systems.

15 Claims, 11 Drawing Sheets

(51) Int. Cl.
*A61B 3/00* (2006.01)
*A61B 3/10* (2006.01)
*A61B 3/12* (2006.01)
*A61B 3/14* (2006.01)

(52) U.S. Cl.
CPC ............... *A61B 3/12* (2013.01); *A61B 3/14* (2013.01); *G06T 3/0068* (2013.01); *H04N 5/23238* (2013.01)

(56) References Cited

U.S. PATENT DOCUMENTS

| | | | |
|---|---|---|---|
| 6,082,859 | A | 7/2000 | Okashita et al. |
| 6,454,410 | B1 | 9/2002 | Berger et al. |
| 6,711,293 | B1 | 3/2004 | Lowe |
| 7,301,644 | B2 | 11/2007 | Knighton et al. |
| 7,426,317 | B2 * | 9/2008 | Nielsen ............... G06T 3/0062 345/629 |
| 7,899,270 | B2 * | 3/2011 | Kim ............... G06T 3/4038 348/97 |
| 7,965,905 | B2 | 6/2011 | Allon et al. |
| 8,073,205 | B2 | 12/2011 | Shinohara |
| 8,126,289 | B2 | 2/2012 | Allon et al. |
| 8,165,401 | B2 | 4/2012 | Funayama et al. |
| 8,194,936 | B2 | 6/2012 | Abramoff et al. |
| 8,224,050 | B2 | 7/2012 | Doering et al. |
| 8,332,016 | B2 | 12/2012 | Stetson |
| 8,356,901 | B2 | 1/2013 | Spaide |
| 8,491,124 | B2 | 7/2013 | Spaide |
| 8,636,364 | B2 | 1/2014 | Spaide |
| 9,177,482 | B1 * | 11/2015 | Reinke ............... G06T 7/62 |
| 9,801,539 | B2 * | 10/2017 | Kerr ............... A61B 3/113 |
| 2005/0089213 | A1 | 4/2005 | Geng |
| 2011/0103655 | A1 | 5/2011 | Young et al. |

OTHER PUBLICATIONS

Can et al., "A Feature-Based Technique for Joint, Linear Estimation of High-Order Image-To-Mosaic Transformations: Mosaicing the Curved Human Retina", IEEE Transactions on Pattern Analysis and Machine Intelligence, vol. 24, No. 3, Mar. 2002, pp. 412-419.

Can et al., "A Feature-Based, Robust, Hierarchical Algorithm for Registering Pairs of Images of the Curved Human Retina", IEEE Transactions on pattern Analysis and Machine Intelligence, vol. 24, No. 3, Mar. 2002, pp. 347-364.

Chen et al., "Comparison of Autophotomontage Software Programs in Eyes with CMV Retinitis", Investigative Ophthalmology & Visual Science, vol. 52, No. 13, Dec. 2011, pp. 9339-9344.

Lee et al., "Feature-Based Pairwise Retinal Image Registration by Radial Distortion Correction", Proc. of SPIE, vol. 6512, 2007, pp. 651220-1-651220-10.

Matsopoulos et al., "Automatic Retinal Image Registration Scheme Using Global Optimization Techniques", IEEE Transactions on Information Technology in Biomedicine, vol. 3, No. 1, Mar. 1999, pp. 47-60.

Stewart et al., "The Dual-Bootstrap Iterative Closest Point Algorithm With Application to Retinal Image Registration", IEEE Transactions on Medical Imaging, vol. 22, No. 11, Nov. 2003, pp. 1379-1394.

Triggs et al., "Bundle Adjustment—A Modern Synthesis", Lecture Notes in Computer Science, vol. 1883, 2000, 71 pages.

* cited by examiner

MONTAGING OF WIDE-FIELD FUNDUS IMAGES

PRIORITY

The present application claims priority to U.S. Provisional Application Ser. No. 62/329,372 filed on Apr. 29, 2016, the contents of which are hereby incorporated by reference in their entirety.

FIELD OF THE INVENTION

This invention generally relates to the field of montaging of fundus images. In particular, the invention discloses a method for montaging two or more wide-field fundus images of an eye while correcting for projective distortion.

BACKGROUND

Montaging of fundus images can aid clinicians by providing a more complete view of the retina. Fundus image montaging is a common technique for extending the imaged field-of-view, and has been offered as a feature on fundus cameras, including the Zeiss VISUCAM® and Heidelberg SPECTRALIS®. Wide-field fundus images (e.g. greater than 45 degrees field of view) are particularly affected by the inherent spherical-to-planar projection during retinal imaging, which results in apparent distortion that makes collating the images into a single mosaic challenging.

Some of the prior-methods (see for example Lee, Sangyeol, Michael D. Abramoff, and Joseph M. Reinhardt. "Feature-based pairwise retinal image registration by radial distortion correction," *Medical Imaging*. International Society for Optics and Photonics, 2007; Can, Ali, et al, "A feature-based, robust, hierarchical algorithm for registering pairs of images of the curved human retina." *Pattern Analysis and Machine Intelligence, IEEE Transactions on* 24.3 (2002): 347-364; and Can, Ali, et al. "A feature-based technique for joint, linear estimation of high-order image-to-mosaic transformations: Mosaicing the curved human retina." *Pattern Analysis and Machine Intelligence, IEEE Transactions on* 24.3 (2002): 412-419, each of which are hereby incorporated by reference) describe ways of applying distortion correction to fundus images in order to improve stitching performance.

In general photography, especially outdoor photography, montaging of panoramic mosaics is performed with consideration of three-dimensional geometry (see for example Brown, Matthew, and David G. Lowe. "Automatic panoramic image stitching using invariant features." *International journal of computer vision* 74, no. 1 (2007): 59-73). Distortion of the camera is considered in this field, but not with particular regard to the optics of the eye.

Here, we present a new technique for creating a panoramic montaged image of two or more wide-field fundus images of an eye while correcting for projection distortion(s) inherent to an imaging system.

SUMMARY

According to an aspect of the subject matter described in the present application, a method creates montages of wide-field fundus images, while correcting for the projective distortion inherent to an imaging system. The methods discussed herein uses specific knowledge of the imaging geometry of the particular imaging system to project fundus images onto a conceptual 3D sphere, which allows them to be stitched together efficiently and precisely. After co-aligning the images using feature detection and matching, the registered images are projected back into 2D to generate the final montaged image. The method could be used on any type of wide-field fundus images including, but not limited to, those generated from optical coherence tomography, optical coherence tomography angiography, and broad-line fundus imaging systems.

Unlike other fundus image montaging methods, this method is particularly advantageous in a number of respects. By way of example and not limitation, this method directly accounts for the projective distortion inherent to the imaging system in order to improve precision. The images are mapped into 3D by calculating 3D ray vectors that are traced to each pixel on the camera. The images are then aligned using either 3D rotations on a conceptual sphere holding the images, or matrix transformation of the re-projected 2D images.

The features and advantages described herein are not all-inclusive and many additional features and advantages will be apparent to one of ordinary skill in the art in view of the figures and description. Moreover, it should be noted that the language used in the specification has been principally selected for readability and instructional purposes and not to limit the scope of the inventive subject matter.

DETAILED DESCRIPTION

All patent and non-patent references cited within this specification are herein incorporated by reference in their entirety to the same extent as if the disclosure of each individual patent and non-patient reference was specifically and individually indicated to be incorporated by reference in its entirely.

System Overview

Example Optical Coherence Tomography (OCT) System

Figure 1:
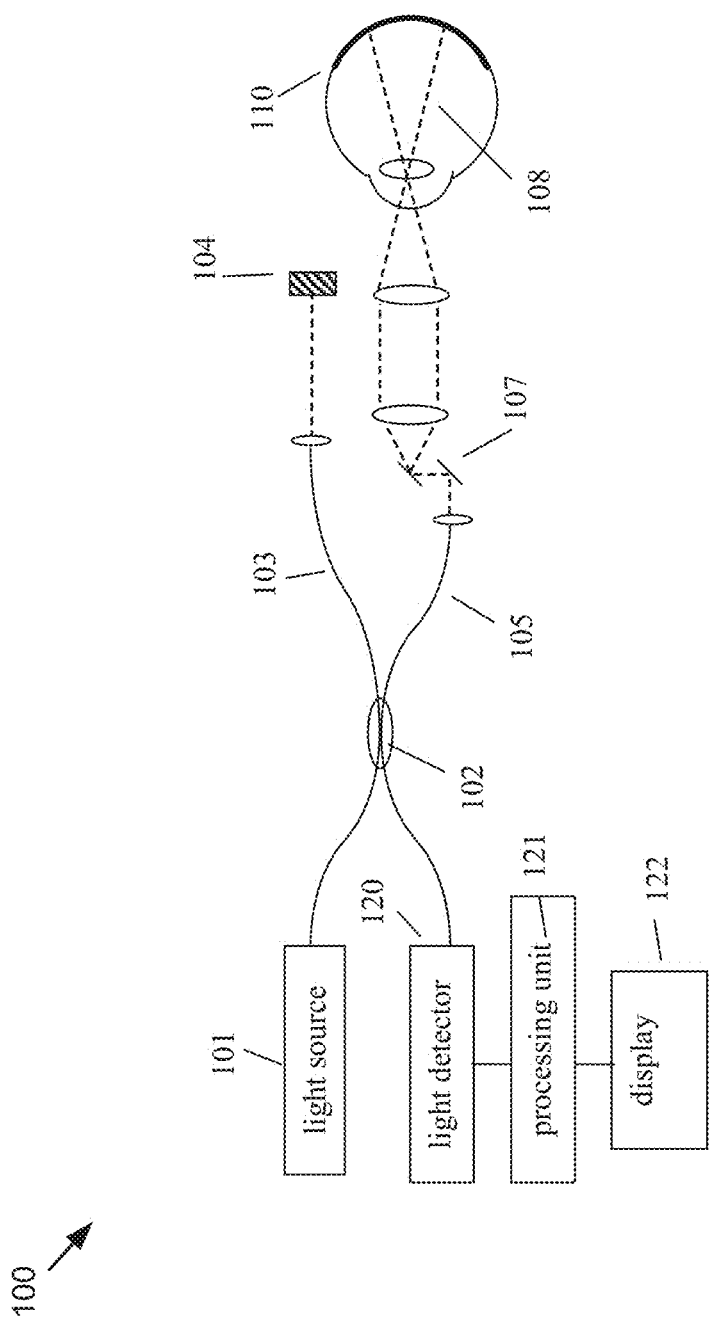
FIG. 1 illustrates one example of an ophthalmic imaging system (specifically, a generalized optical coherence tomography (OCT) system) that can be used to practice the present invention.
Figure 10:
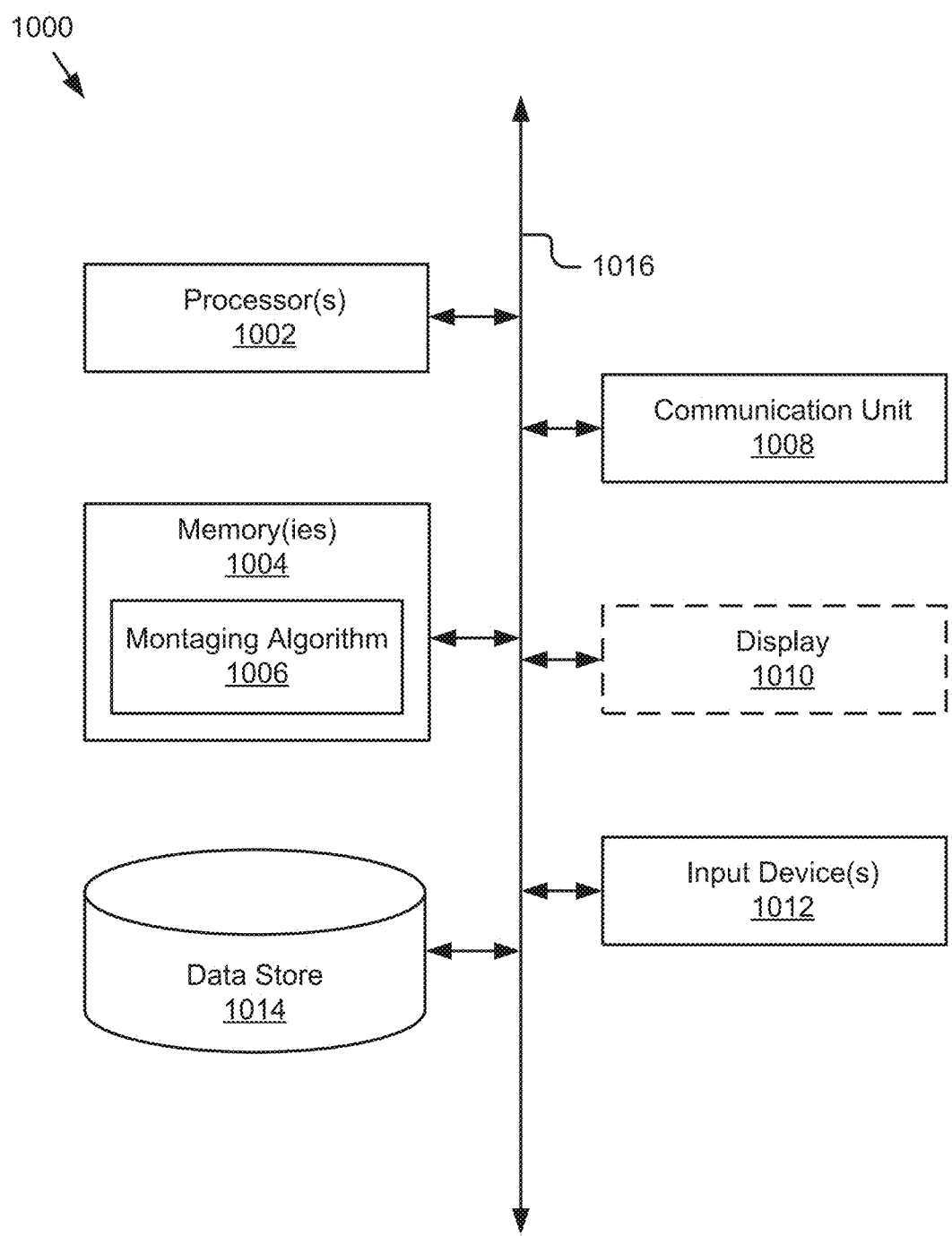
FIG. 10 is a block diagram of a general computer system that may perform the functions discussed in this disclosure according to one aspect of the present invention.

A generalized FD-OCT system used to collect 3-D image data of the eye suitable for use with the present invention is illustrated in FIG. 1. A FD-OCT system 100 includes a light source, 101, typical sources including but not limited to broadband light sources with short temporal coherence lengths or swept laser sources. A beam of light from source 101 is routed, typically by optical fiber 105, to illuminate the sample 110, a typical sample being tissues in the human eye. The source 101 can be either a broadband light source with short temporal coherence length in the case of SD-OCT or a wavelength tunable laser source in the case of SS-OCT. The light is scanned, typically with a scanner 107 between the output of the fiber and the sample, so that the beam of light (dashed line 108) is scanned laterally (in x and y) over the region of the sample to be imaged. Light scattered from the sample is collected, typically into the same fiber 105 used to route the light for illumination. Reference light derived from the same source 101 travels a separate path, in this case involving fiber 103 and retro-reflector 104 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 102, to form light interference in a detector 120. Although a single fiber port is shown going to the detector, those skilled in the art recognize that various designs of interferometers can be used for balanced or unbalanced detection of the interference signal. The output from the detector 120 is supplied to a processor 121 that converts the observed interference into depth information of the sample. The results can be stored in the processor 121 or other storage medium or displayed on display 122. The processing and storing functions may be localized within the OCT instrument or functions may be performed on an external processing unit (e.g., computer system 1000 as shown in FIG. 10) to which the collected data is transferred. This unit could be dedicated to data processing or perform other tasks which are quite general and not dedicated to the OCT device. The processor 121 may contain for example a field-programmable gate array (FPGA), a digital signal processor (DSP), an application specific integrated circuit (ASIC), a graphics processing unit (GPU), a system on chip (SoC) or a combination thereof, that performs some, or the entire data processing steps, prior to passing on to the host processor or in a parallelized fashion.

The interference causes the intensity of the interfered light to vary across the spectrum. The Fourier transform of the interference light reveals the profile of scattering intensities at different path lengths, and therefore scattering as a function of depth (z-direction) in the sample. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. A variety of ways to create B-scans are known to those skilled in the art including but not limited to along the horizontal or x-direction, along the vertical or y-direction, along the diagonal of x and y, or in a circular or spiral pattern. A volume of 3D data can be processed to generate wide field fundus images (i.e., en face images) by assigning a single representative value for the intensity values (e.g. summation, integration, median value, minimum value, etc.) in all or a portion of the volume along an axis of the volume (see for example U.S. Pat. Nos. 7,301,644 and 8,332,016 hereby incorporated by reference).

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system.

The OCT system may use any one of a number of OCT Angiography processing algorithms on OCT data collected at the same or approximately the same transverse locations on a sample at different times to identify and/or visualize regions of motion or flow. A typical OCT angiography data set contains multiple scans repeated at the same transverse locations. Motion contrast algorithms can be applied to the intensity information derived from the image data (intensity-based algorithm), the phase information from the image data (phase-based algorithm), or the complex image data (complex-based algorithm). An en face vasculature image is an image displaying motion contrast signal in which the data dimension corresponding to depth is displayed as a single representative value, typically by summing or integrating all or an isolated portion of the data as described above.

The OCT system discussed herein may provide 2D (i.e. cross-sectional) images, en-face images, 3-D images, metrics related to a health condition, and the like. This system may be used with any other system. The OCT system may be used to analyze any sample.

Example Broad-Line Fundus Imaging (BLFI) System

Figure 2:
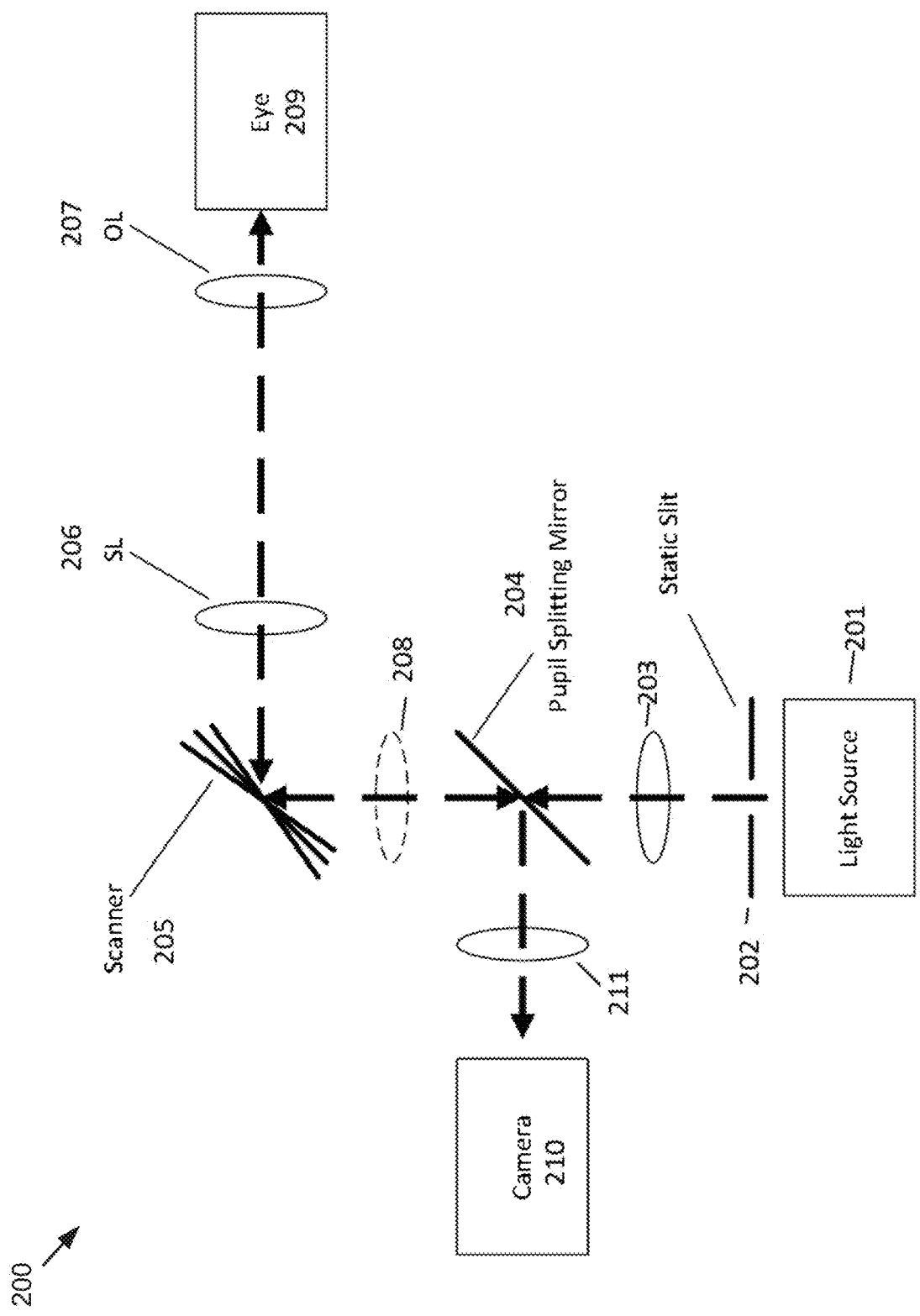
FIG. 2 illustrates another example of an ophthalmic imaging system (specifically, a generalized broad-line fundus imaging (BLFI) system) that can be used to practice the present invention.

FIG. 2 illustrates basic components of a BLFI system 200 capable of generating wide-field fundus images. As depicted, the system 200 includes one or more light sources 201, preferably a multi-color LED system or a laser system in which the etendue has been suitably adjusted. An adjustable slit 202 is positioned in front of the light source 201 to determine the illumination line width. This could also be established by the source independent of a slit or aperture. In the embodiment shown on FIG. 2, the slit 202 remains static during the imaging but can be adjusted to different widths to allow for different confocality levels and different applications either for a particular scan or during the scan for use in suppressing reflexes. An objective lens 203 forms a pupil of the slit. The objective lens 203 can be any one of state of the art lenses including but not limited to refractive, diffractive, reflective, or hybrid lenses/systems. The light passes through a pupil splitting mirror 204 and is directed towards a scanner 205. It is desirable to bring the scanning plane and the pupil plane as near together as possible to reduce vignetting in the system. Optional optics 208 may be included to manipulate the optical distance between the images of the two components. The main task of the pupil splitter 204 is to combine and split the illumination and detection beams and to aid in the suppression of system reflexes. The scanner 105 could be a rotating galvo scanner or other types of scanners (i.e. piezo or voice coil). Depending on whether the pupil splitting is done before or after the scanner, the scanning could be broken into two steps wherein one scanner is in the illumination path and a separate scanner is in the detection path.

From the scanner, the light passes through one or more optics, in this case a scanning lens (SL) 206 and an ophthalmic or ocular lens (OL) 207, that allow for the pupil of the eye 209 to be imaged to an image pupil of the system. One possible configuration for these optics is a Kepler type telescope wherein the distance between the two lenses is selected to create an approximately telecentric intermediate fundus image (4-f configuration). The ophthalmic lens 207 could be a single lens, an achromatic lens or an arrangement of different lenses. All lenses could be refractive, diffractive, reflective or hybrid as known to one skilled in the art. The focal length(s) of the ophthalmic lens 207, scan lens 206 and the size and/or form of the pupil splitting 204 and scanning mirrors 205 could be different depending on the desired field of view (FOV), and so an arrangement in which multiple components can be switched in and out of the beam path, for example by using a flip in optic, a motorized wheel, or a detachable optical element, depending on the field of view can be envisioned. Since the field of view change results in a different beam size on the pupil, the pupil splitting can also be changed in conjunction with the change to the FOV. It is possible to have a 45°-60° field of view as is typical for fundus cameras. Higher fields of view (60°-120°) may be desired for a combination of the BLFI with other imaging modalities such as optical coherence tomography (OCT). The upper limit for the field of view will be determined by the accessible working distance in combination with the physiological conditions around the human eye. Because a typical human retina has a FOV of 140° horizontal and 80°-100° vertical, it may be desirable to have an asymmetrical field of view for the highest possible FOV on the system.

The light passes through the pupil of the eye 209 and is directed towards the retinal surface. The scanner 205 adjusts the location of the light on the retina or fundus such that a range of transverse locations on the eye are illuminated. Reflected or scattered light (or emitted light in the case of fluorescence imaging) is directed back along the same path as the illumination. At the pupil splitting mirror 204, the reflected light is separated from the illumination light and directed towards a camera 210. An objective lens 211 exists in the detection path to image the fundus to the camera 210. As is the case for objective lens 203, objective lens 211 could be any type of refractive, diffractive, reflective or hybrid lens as is known by one skilled in the art.

In some embodiments, the camera 210 can be connected to a processor (not shown) and a display (not shown). The processing and displaying modules can be included with the system 200 itself or on a dedicated processing and displaying unit, such as the computer system 1000 (see FIG. 10), wherein data is passed from the camera 210 to the computer system 1000 over a cable or network including wireless networks. The display (not shown) can include a user interface for displaying information to and receiving information from an instrument operator or user. For de-scanned systems (e.g., de-scanned system 200) in which the image is built up in part, the processor (not shown) is responsible for combining or mosaicking the multiplicity of images collected while stepping the scanner and combining them into a single image, as discussed in further detail below.

Wide-Field Fundus Images Montaging Algorithm

The algorithm for montaging wide-field fundus images is hereby described with reference to the two implementation methods shown in FIGS. 3a and 3b. Both implementations involve projecting the 2D images into a three dimensional (3D) space by mapping the pixels to 3D ray vectors and performing feature detection and matching on the images. The mapping of pixels accounts for the optical distortion of the system. Typically a fundus camera has a relation such as:

$$\begin{pmatrix} p_x \\ p_y \end{pmatrix} = M \begin{pmatrix} \cos\varphi \\ \sin\varphi \end{pmatrix}(\sin\theta + D(\theta))$$

between pixel locations $p_x$, $p_y$, ray angles $\theta$, and ray azimuth $\varphi$, where M is magnification and D ($\theta$) is a distortion correction term. Similar relationships would be known to one skilled in the art. We encode the ray angles as unit vectors and place the pixels and their image data onto the unit sphere It should be understood that the methods described herein are not limited to the steps and/or operations referenced in these figures and that other steps and/or operations are also possible and are within the scope of the present disclosure. It should also be understood that not every step described herein must be performed and that in some cases the steps may be performed in different orders than pictured.

First Implementation Approach

Figure 3A:
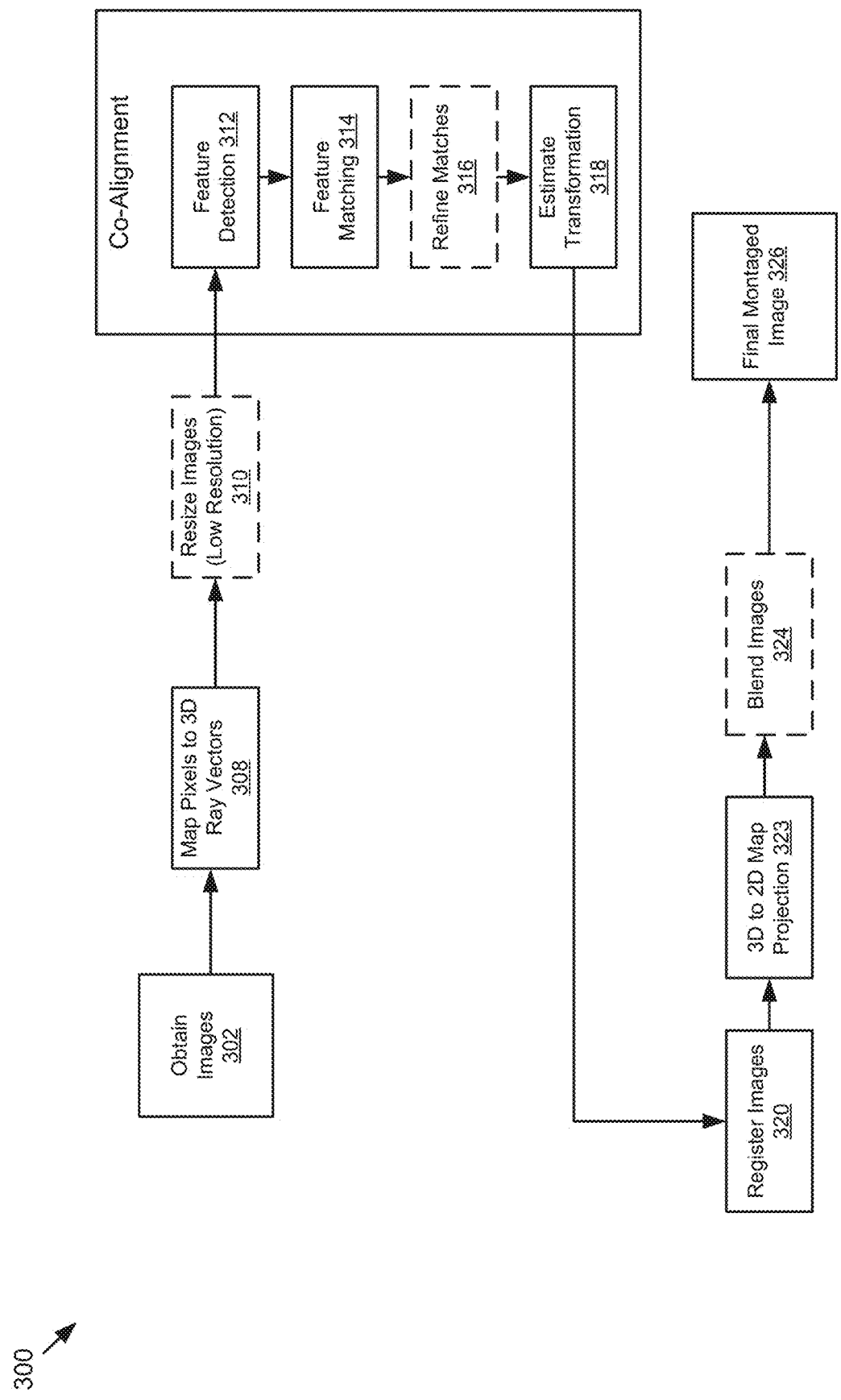
FIG. 3a is a flowchart of an example method for wide-field fundus montaging according to one aspect of the present invention.

In this first implementation illustrated in FIG. 3a, the center of the image sensor is considered as the center of projection from 2D image space to a 3D sphere. The relative pitch, yaw, and roll of the conceptual 3D spheres holding the images are iteratively adjusted and then the feature-points are re-projected to the common projection plane. The specific steps of method 300 will now be described in detail in reference to FIG. 3a.

Figure 4:
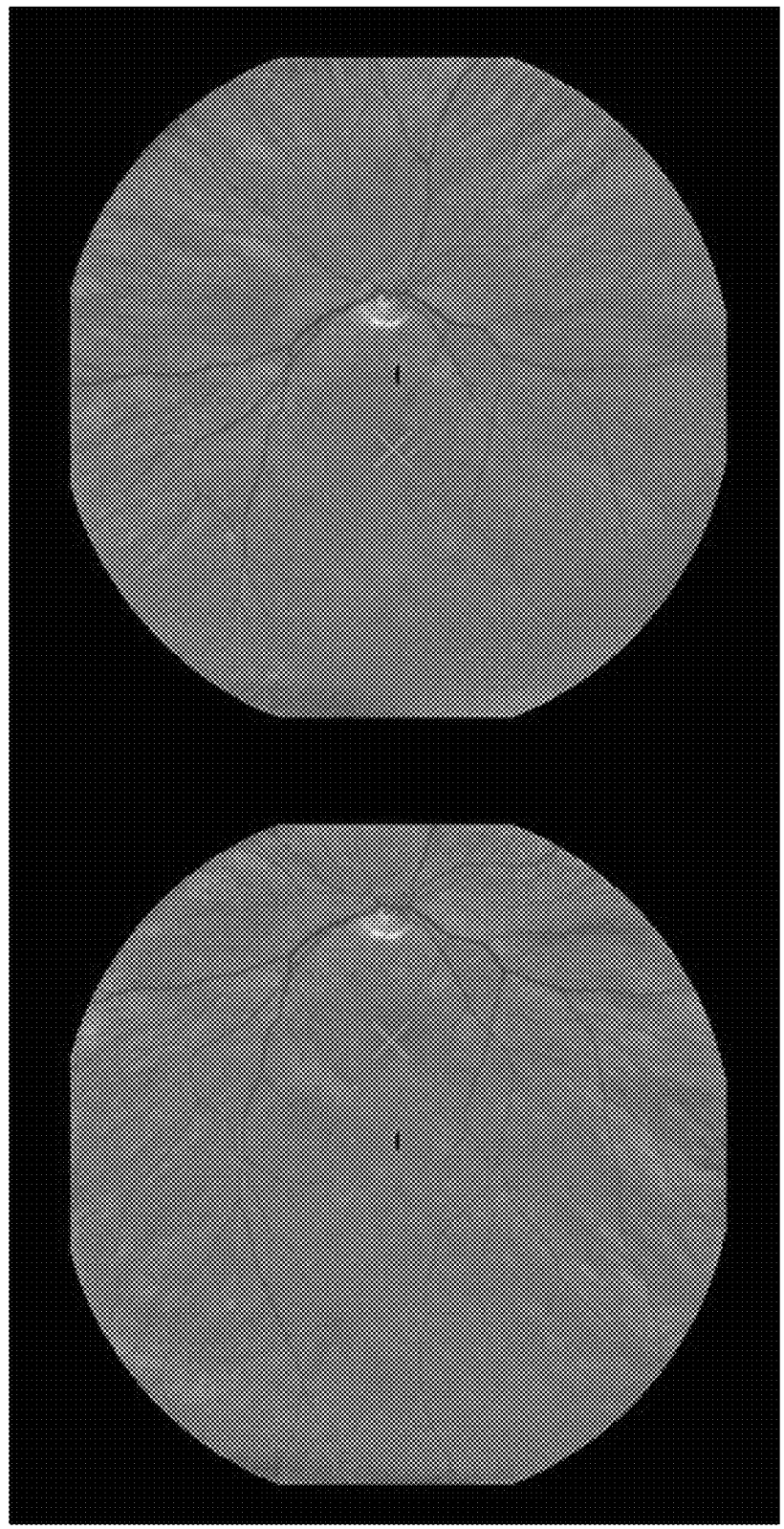
FIG. 4 shows a pair of wide-field fundus images obtained with a fixation target position temporally (left) and nasally (right). The X indicates an estimated foveal position.
Figure 5:
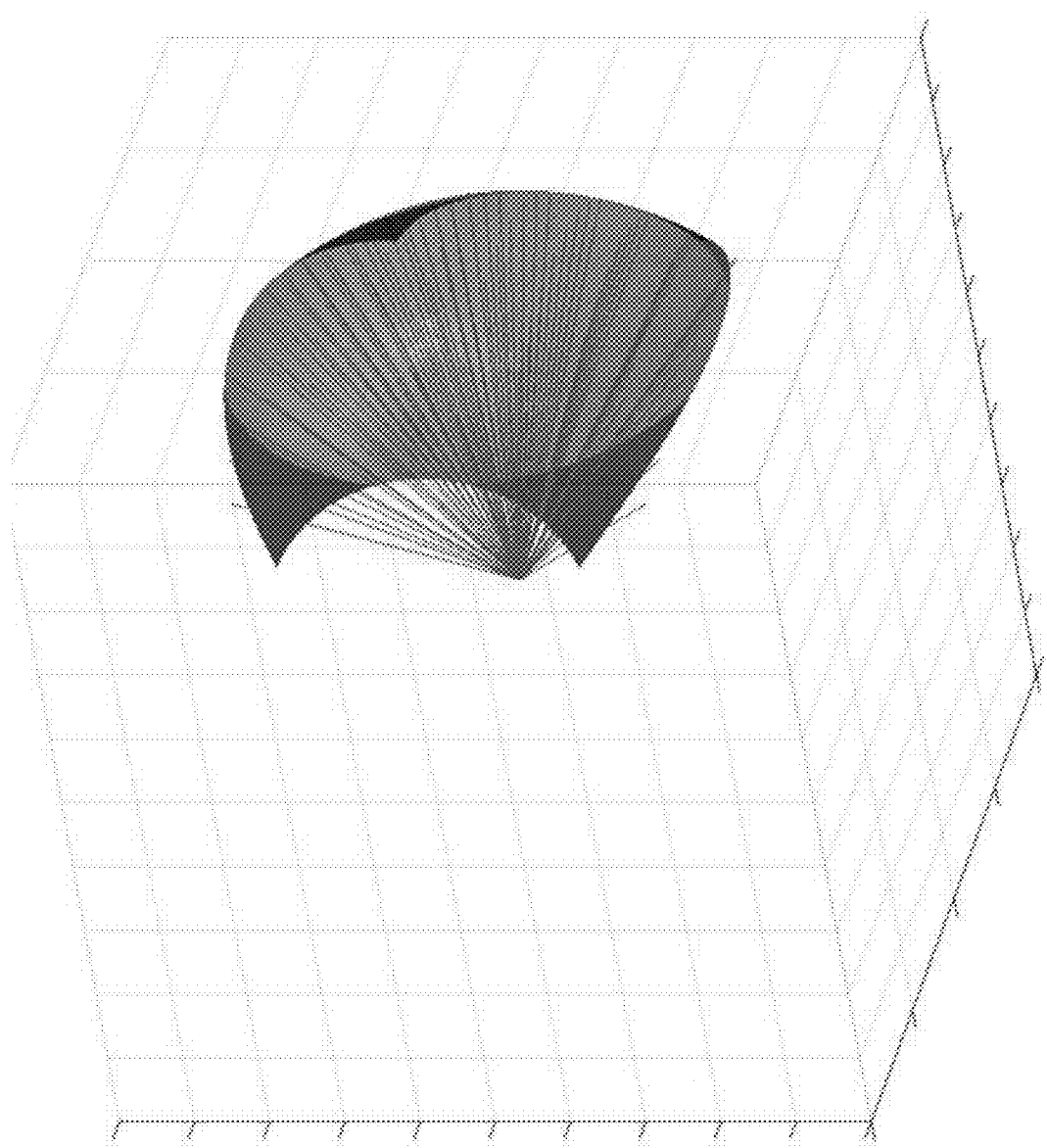
FIG. 5 shows an example of 3D mapping of a fundus image onto a unit sphere with ray vectors originating from the origin traced to the image pixels.

In block 302, two or more wide-field fundus images (see for example, FIG. 4) are obtained with a broad-line opthalmoscope, such as the BLFI system 200 shown in FIG. 2. The images may be taken with differing fixation positions. Next, in block 308, a mapping between each of the fundus images and a set of 3D ray vectors is established that maps each location on the fundus image to a point on a 3D sphere of unit ray vectors as illustrated in FIG. 5. We encode the ray angles as unit vectors and place the pixels and their image data onto a unit sphere. The images can be optionally resized if desired (block 310).

Figure 7:
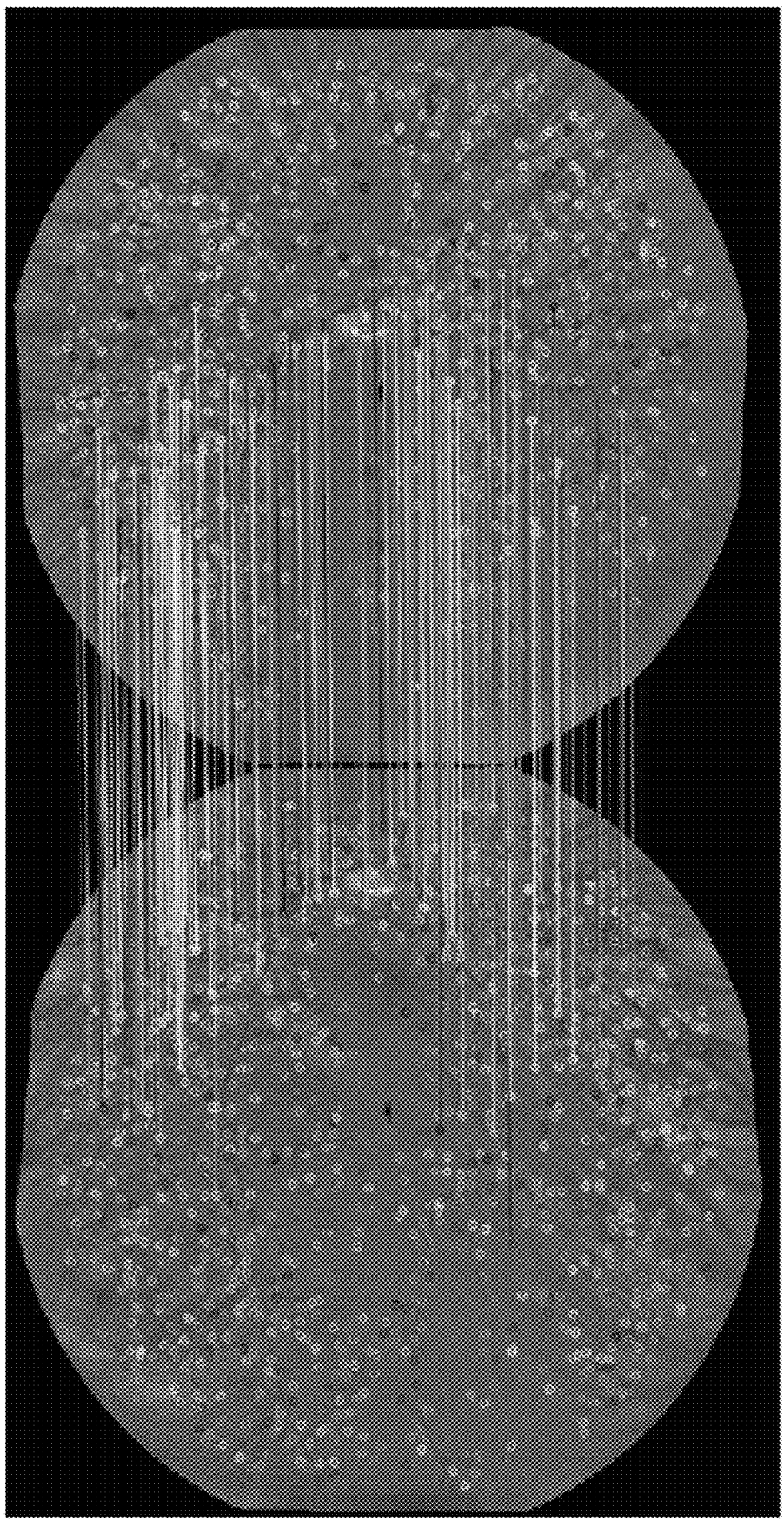
FIG. 7 shows an example of feature detection and matching between two images where detected features are shown by dots and matched features are connected by lines.
Figure 8:
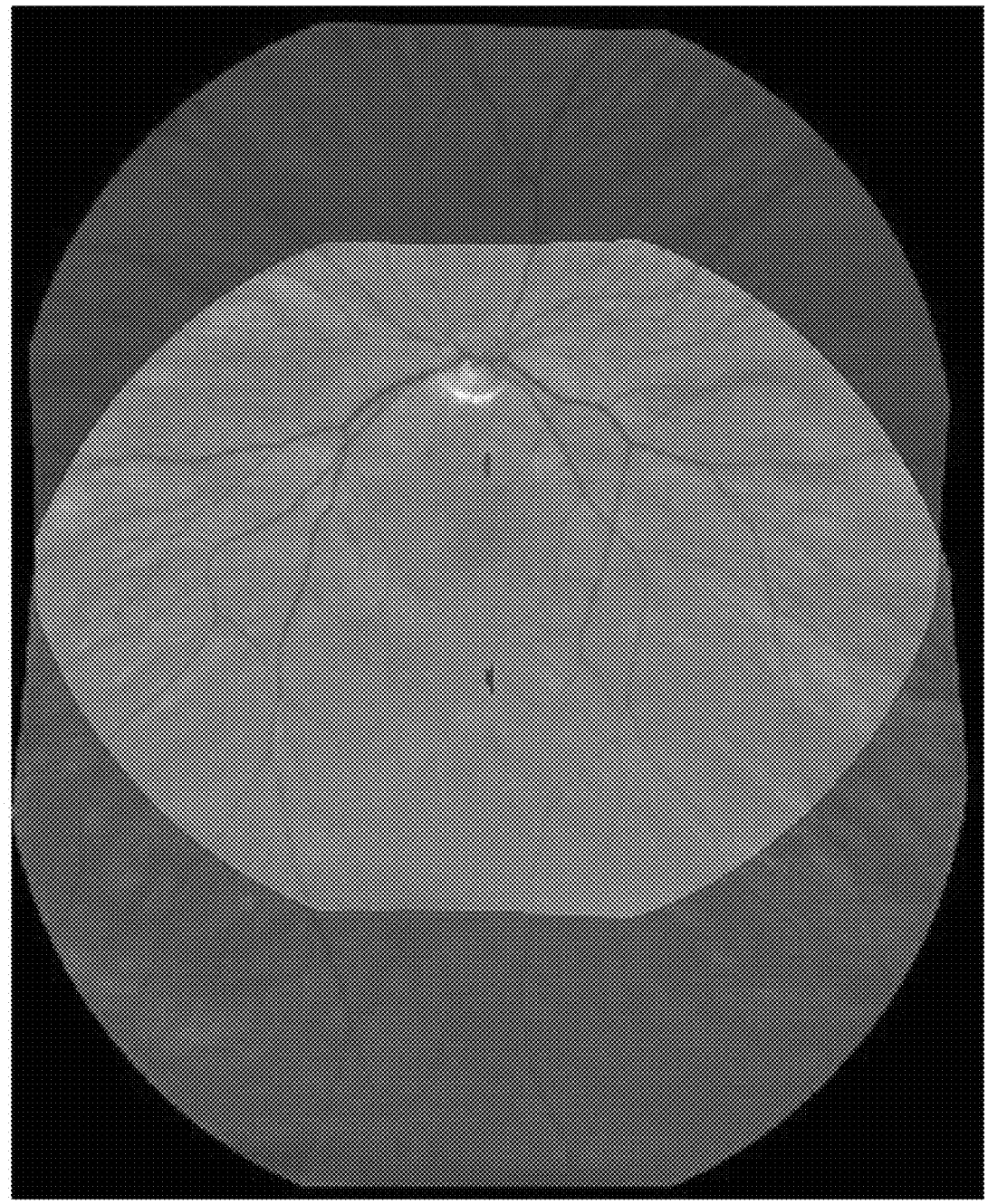
FIG. 8 shows an example of a composite image.

Next, features are detected (block 312) and then matched (block 314) in each of the images (see for example, FIG. 7) using standard image processing methods known in the art. The matched features may optionally be refined (block 316) using a random sample consensus (RANSAC) method. Using the matched image features, in block 318, a transformation model is determined. This enables the images to be registered (block 320). This can be accomplished by computing an overlap between the two images. In a preferred implementation, the transformation and registration is computed according to minimization of a cost function based upon the distances between matched feature points. An example of a composite of two registered images is shown in FIG. 8. The registered images are then re-projected into a common output 2D space (323), using the 3D ray vectors and any preferred geometrical map projection. The choice of projection may be made for aesthetic reasons or to preserve some measure for subsequent analysis (e.g. area or shape).

Figure 9:
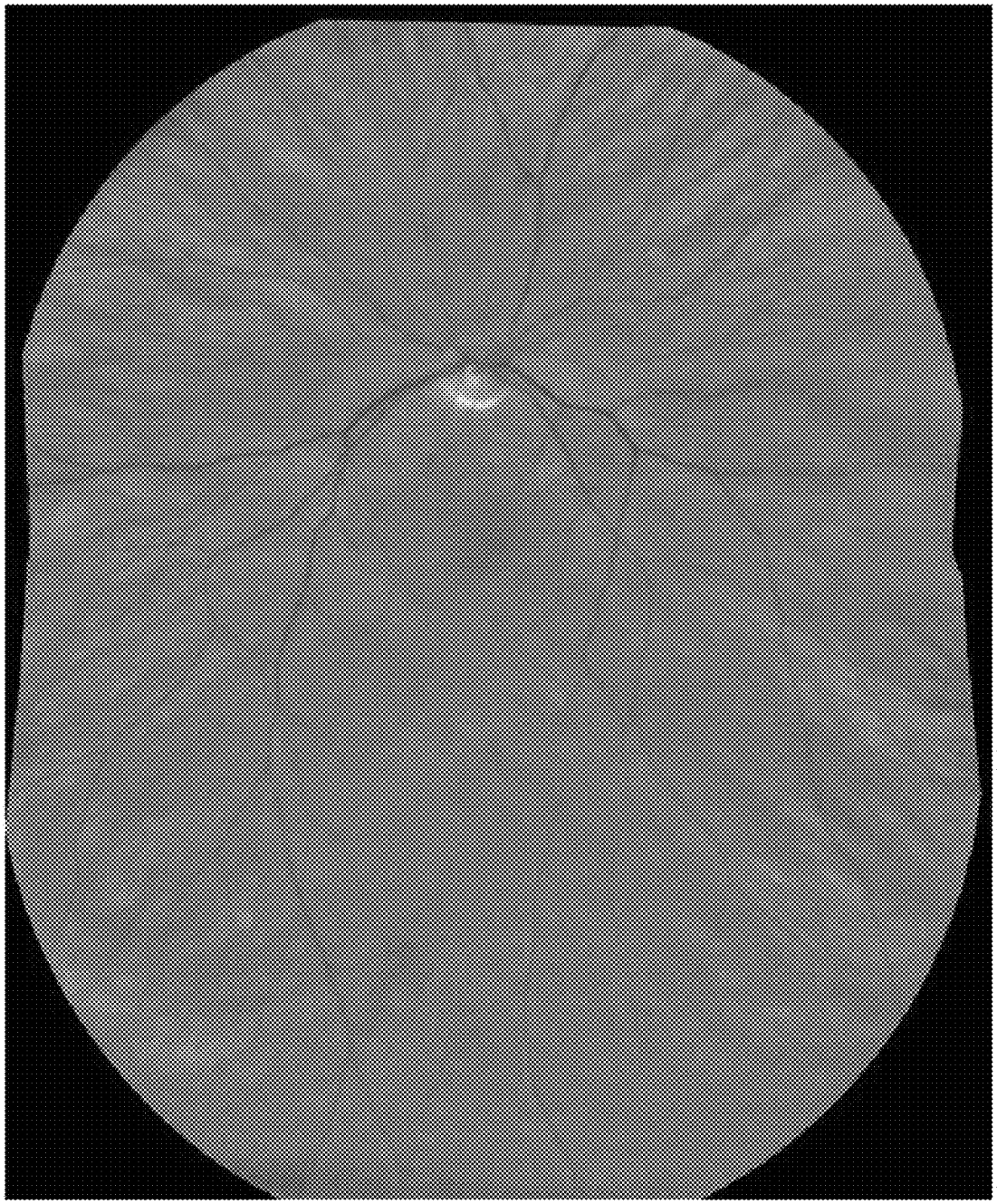
FIG. 9 shows an example of a final montage of a fundus image pair.

Next, in block 324, an optional blending method is used (e.g., a simple linear blending, though any other blending method could be used) for combining the aligned images to obtain a final montaged image (326), as shown for example in FIG. 9. This image can be displayed on a display or further analyzed in the processor.

Second Implementation Approach

Figure 3B:
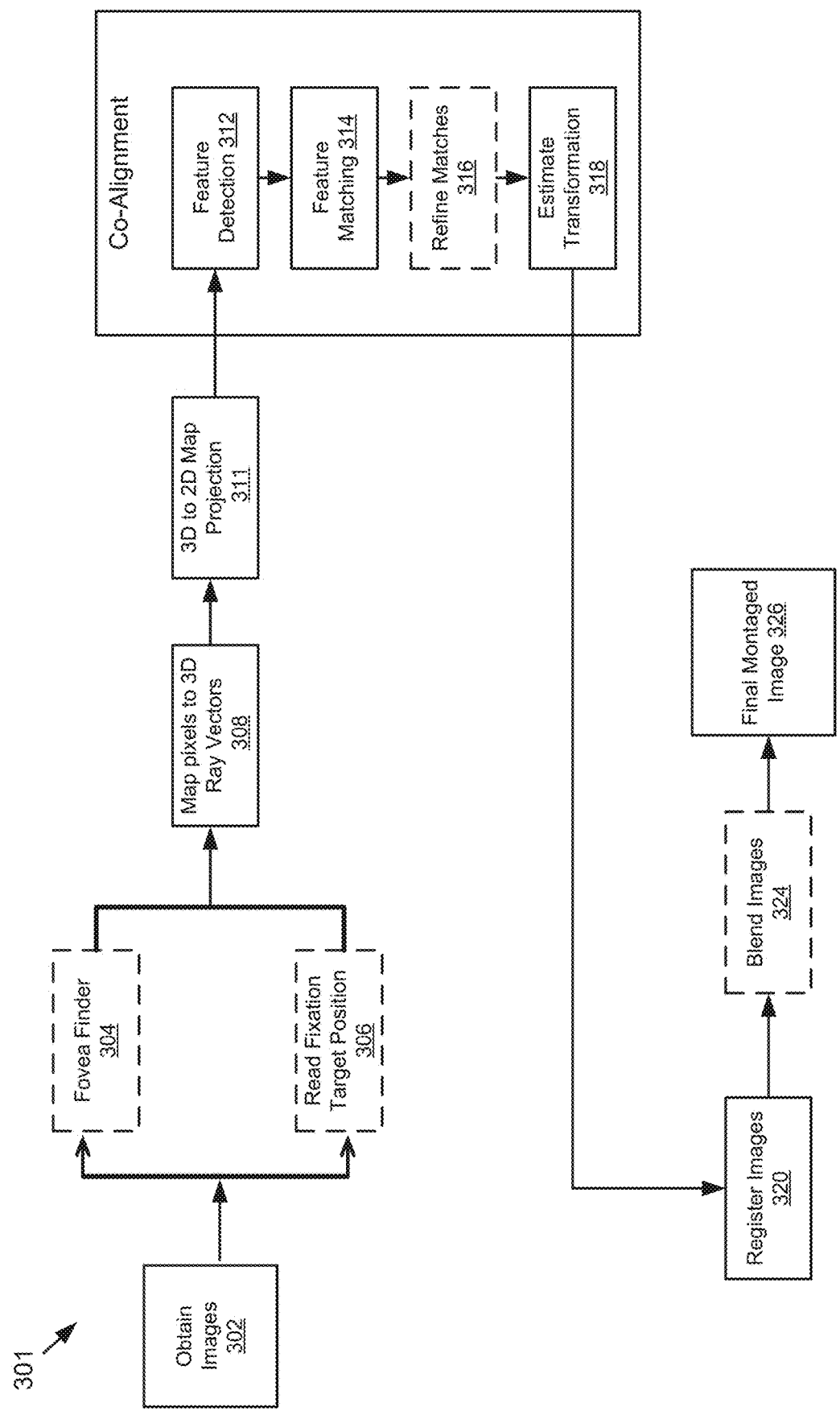
FIG. 3b is a flowchart of an example method for wide-field fundus montaging according to a second aspect of the present invention.

In this approach illustrated in FIG. 3b, all constituent images are separately mapped onto the 3D sphere and then projected back onto a common projection plane normal to a common feature or point in both images, for example the found fovea. There the images undergo feature detection and stitching using a standard 2D matrix transformation model known in the art. This approach has the advantage of not requiring an optimization step, and being more easily scalable. However, it is likely to be less precise than the first approach (discussed above) because it uses only the approximate orientation based on found fovea locations to project 3D ray vectors to the common projection plane, such that any changes in distortion that should follow from the fine alignment of the image are negligible, and saving the limited perspective-correction that is part of the 2D matrix transform. The method 301 will now be described in detail in reference to FIG. 3b.

In block 302, two wide-field fundus images (see for example, FIG. 4) are obtained with a broad-line opthalmoscope, such as the BLFI system 200 shown in FIG. 2. The images may be taken with differing fixation positions. In a first step, a common location or point in each of the images is identified. This common location may be the fovea, the center of the patient's fixation. In a first embodiment, the center of fixation is detected using a fovea-finding algorithm (block 304). Alternatively, readout of the fixation target position from the system can be used to determine the center of fixation (block 306). In the next step, a mapping between each of the fundus images and a set of 3D ray vectors is established that maps each location on the fundus image to a point on a 3D sphere of unit ray vectors as illustrated in FIG. 5. We encode the ray angles as unit vectors and place the pixels and their image data onto the unit sphere. The identification of a common location in the two images (blocks 304 or 306) can happen before or after the 3D mapping step (block 308), but in a preferred embodiment, the fovea is identified first and the images are aligned on the 3D spheres according to their relative fixation positions as shown for example in FIG. 6. Next we project each of the fundus images onto a two-dimensional (2D) space using the 3D ray vectors and the common locations (block 311).

Figure 6:
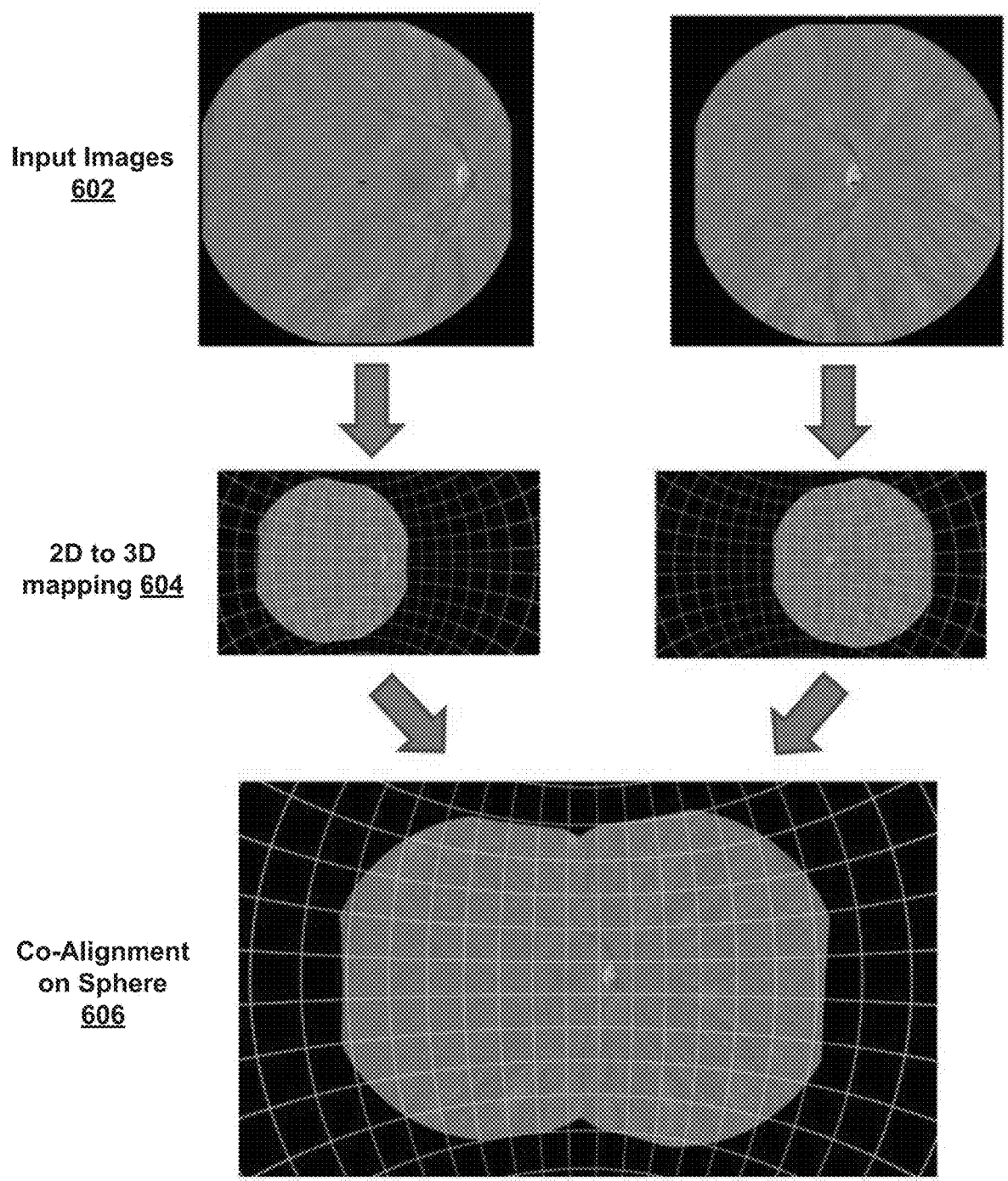
FIG. 6 shows an example of an alignment of a 3D mapped fundus images onto unit spheres in 3D.

Next, analogous to the first implementation, features are detected (block 312) and then matched (block 314) in each of the images (see for example, FIG. 7) using standard image processing methods known in the art. The matched features may optionally be refined (block 316) using a random sample consensus (RANSAC) method. Using the matched image features, in block 318, a transformation model is determined. This enables the images to be registered (block 320). In this implementation, the transformation and registration incorporate a re-projection of the images to 2D space, whereby a standard 2D matrix transformation model known in the art is utilized. The second implementation approach is less computationally complex than the first, but is likely to yield a less precise alignment of the images Portions of the first implementation approach is illustrated in FIG. 6. Image data (602) are projected from 2D into 3D (604) (each sphere freely pitched, yawed, and rolled) and then after registration based on matched features identified between the two images, are projected onto a 2D plane (606).

Next, in block 324, an optional blending method is used (e.g., a simple linear blending, though any other blending method could be used) for combining the aligned images to obtain a final montaged image (326), as shown for example in FIG. 9. This image can be displayed on a display or further analyzed in the processor.

It should be understood that the montaging algorithm discussed above is not limited to montaging of two images and multiple images can be montaged using the steps discussed with respect to the methods 300 or 301. For multiple images, the feature matching can be done pairwise image-by-image or, preferably, the rigid-body angles of all images can be refined for best alignment via a single optimization problem known in the art (see for example, Triggs, B., et al. (2000). "Bundle Adjustment—A Modern Synthesis." Volume 1883).

It should further be noted that a similar algorithm may be used for any type of montaging where projective distortion is significant. For example, such an algorithm may be useful for OCT and OCT angiography images, particularly for wider field scans.

Example Computer System

The processing unit 121 that has been discussed herein in reference to the OCT system 100 in FIG. 1 and/or the processor/processing unit (not shown) that has been discussed in reference to the BLFI system in 200 can be implemented with a computer system configured to perform the functions that have been described herein for these units. For instance, each of these processing units can be implemented with the computer system 1000, as shown in FIG. 10. The computer system 1000 may include one or more processors 1002, one or more memories 1004, a communication unit 1008, an optional display 1010, one or more input devices 1012, and a data store 1014. The display 1010 is shown with dotted lines to indicate it is an optional component, which, in some instances, may not be a part of the computer system 1000. In some embodiments, the display 1010 is the display 122 that has been discussed in reference to FIG. 1 or the display referenced in FIG. 2.

The components 1002, 1004, 1008, 1010, 1012, and 1014 are communicatively coupled via a communication or system bus 1016. The bus 1016 can include a conventional communication bus for transferring data between components of a computing device or between computing devices. It should be understood that the computing system 1000 described herein is not limited to these components and may include various operating systems, sensors, video processing components, input/output ports, user interface devices (e.g., keyboards, pointing devices, displays, microphones, sound reproduction systems, and/or touch screens), additional processors, and other physical configurations.

The processor(s) 1002 may execute various hardware and/or software logic, such as software instructions, by performing various input/output, logical, and/or mathematical operations. The processor(s) 1002 may have various computing architectures to process data signals including, for example, a complex instruction set computer (CISC) architecture, a reduced instruction set computer (RISC) architecture, and/or architecture implementing a combination of instruction sets. The processor(s) 1002 may be physical and/or virtual, and may include a single core or plurality of processing units and/or cores. In some embodiments, the processor(s) 1002 may be capable of generating and providing electronic display signals to a display device, such as the display 1010, supporting the display of images, capturing and transmitting images, performing complex tasks including various types of feature extraction and sampling, etc. In some embodiments, the processor(s) 1002 may be coupled to the memory(ies) 1004 via a data/communication bus to access data and instructions therefrom and store data therein. The bus 1016 may couple the processor(s) 1002 to the other components of the computer system 1000, for example, the memory(ies) 1004, the communication unit 1008, or the data store 1014.

The memory(ies) 1004 may store instructions and/or data that may be executed by the processor(s) 1002. In the depicted embodiment, the memory(ies) 1004 stores at least a montaging algorithm 1006, such as the wide-field fundus images montaging algorithm discussed above, which may include software, code, logic, or routines for performing any and/or all of the techniques described herein. For instance, the montaging algorithm 1006 may perform all or some of the steps/operations depicted in FIG. 3. In some embodiments, the memory(ies) 1004 may also be capable of storing other instructions and data including, for example, an operating system, hardware drivers, other software applications, databases, etc. The memory(ies) 1004 are coupled to the bus 1016 for communication with the processor(s) 1002 and other components of the computer system 1000. The memory(ies) 1004 may include a non-transitory computer-usable (e.g., readable, writeable, etc.) medium, which can be any apparatus or device that can contain, store, communicate, propagate or transport instructions, data, computer programs, software, code, routines, etc. for processing by or in connection with the processor(s) 1002. A non-transitory computer-usable storage medium may include any and/or all computer-usable storage media. In some embodiments, the memory(ies) 1004 may include volatile memory, non-volatile memory, or both. For example, the memory(ies) 1004 may include a dynamic random access memory (DRAM) device, a static random access memory (SRAM) device, flash memory, a hard disk drive, a floppy disk drive, a CD ROM device, a DVD ROM device, a DVD RAM device, a DVD RW device, a flash memory device, or any other mass storage device known for storing instructions on a more permanent basis.

The computer system 1000 may include one or more computers or processing units at the same or different locations. When at different locations, the computers may be configured to communicate with one another through a wired and/or wireless network communication system, such as the communication unit 1008. The communication unit 1008 may include network interface devices (I/F) for wired and wireless connectivity. For example, the communication unit 1008 may include a CAT-type interface, USB interface, or SD interface, transceivers for sending and receiving signals using Wi-Fi™; Bluetooth®, or cellular communications for wireless communication, etc. The communication unit 1008 can link the processor(s) 1002 to a computer network that may in turn be coupled to other processing systems.

The display 1010 represents any device equipped to display electronic images and data as described herein. The display 1010 may be any of a conventional display device, monitor or screen, such as an organic light-emitting diode (OLED) display, a liquid crystal display (LCD). In some embodiments, the display 1010 is a touch-screen display capable of receiving input from one or more fingers of a user. For example, the device 1010 may be a capacitive touch-screen display capable of detecting and interpreting multiple points of contact with the display surface.

The input device(s) 1012 are any devices for inputting data on the computer system 1000. In some embodiments, an input device is a touch-screen display capable of receiving input from one or more fingers of the user. The functionality of the input device(s) 1012 and the display 1010 may be integrated, and a user of the computer system 1000 may interact with the system by contacting a surface of the display 1010 using one or more fingers. In other embodiments, an input device is a separate peripheral device or combination of devices. For example, the input device(s) 1012 may include a keyboard (e.g., a QWERTY keyboard) and a pointing device (e.g., a mouse or touchpad). The input device(s) 1012 may also include a microphone, a web camera, or other similar audio or video capture devices.

The data store 1014 can be an information source capable of storing and providing access to data. In the depicted embodiment, the data store 1014 is coupled for communication with the components 1002, 1004, 1008, 1010, and 1012 of the computer system 1000 via the bus 1016, and coupled, via the processor(s) 1002, for communication with the montaging algorithm 1006. In some embodiments, the montaging algorithm 1006 is configured to manipulate, i.e., store, query, update, and/or delete, data stored in the data store 1014 using programmatic operations.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. As will be understood by those familiar with the art, the present subject matter may be embodied in other specific forms without departing from the spirit or essential characteristics thereof. Furthermore, it should be understood that the modules, routines, features, attributes, methodologies and other aspects of the present subject matter can be implemented using hardware, firmware, software, or any combination of the three.

The invention claimed is:

1. A method for creating a panoramic montaged image of the retina of an eye, said method comprising:
    obtaining two or more fundus images from an ophthalmic imaging system;
    mapping the two or more fundus images onto a set of three-dimensional (3D) ray vectors where the vectors include information regarding the optical distortion of the ophthalmic imaging system;
    identifying a common location in each of the two or more fundus images;
    projecting each of the two or more fundus images onto a two-dimensional (2D) space using the 3D ray vectors and the common locations;
    detecting and matching features between the two or more projected fundus images;
    estimating a transformation between the two or more projected images using the detected and matched features;
    registering the two projected images using the estimated transformation; and creating the panoramic montaged image of the retina by compositing the projected registered images in the 2D space.

2. The method as recited in claim 1, wherein the identifying a common location in each of the two or more fundus images involves using a fovea-finding algorithm on each fundus image to find the fovea in each image.

3. The method as recited in claim 1, wherein each fundus image includes a stored position of a fixation target and the identifying a common location in each of the two or more fundus images includes extracting the stored position of the fixation target from each images.

4. The method as recited in claim 1, wherein the ophthalmic imaging system is an optical coherence tomography (OCT) system.

5. The method as recited in claim 1, wherein the ophthalmic imaging system is a broad lined fundus imaging (BLFI) system.

6. The method as recited in claim 1, wherein said step of creating the panoramic montaged image comprises computing an overlap between the aligned images and blending the aligned images.

7. The method as recited in claim 1, wherein the two or more fundus images are obtained with differing fixation positions.

8. The method as recited in claim 1, wherein the estimating and registering steps include re-projecting the two or more fundus images to a 2D space whereby a standard 2D matrix transformation model is used.

9. A method for creating a panoramic montaged image of the retina of an eye, said method comprising:
   obtaining two or more fundus images from an ophthalmic imaging system;
   mapping the two or more fundus images onto a set of three-dimensional (3D) ray vectors where the vectors include information regarding the optical distortion of the ophthalmic imaging system;
   detecting and matching features between the two or more fundus images;
   estimating a transformation between the two or more images using the detected and matched features;
   registering the two images using the estimated transformation;
   projecting the registered images onto a two-dimensional (2D) space using the 3D ray vectors; and
   creating the panoramic montaged image of the retina by compositing the projected registered images; and
   storing or displaying the panoramic montaged image or a further analysis thereof.

10. The method as recited in claim 9, wherein the ophthalmic imaging system is an optical coherence tomography (OCT) system.

11. The method as recited in claim 9, wherein the ophthalmic imaging system is a broad line fundus imaging (BLFI) system.

12. The method as recited in claim 9, wherein said step of creating the panoramic montaged image comprises computing an overlap between the aligned images and blending the aligned images.

13. The method as recited in claim 9, wherein the two or more fundus images are obtained with differing fixation positions.

14. The method as recited in claim 9, further comprising resizing the fundus images prior to the detecting and matching step.

15. The method as recited in claim 9, wherein the estimating and registering steps involve minimizing a cost function based upon the distances between matched feature points.

* * * * *

UNITED STATES PATENT AND TRADEMARK OFFICE
CERTIFICATE OF CORRECTION

PATENT NO. : 10,512,395 B2  
APPLICATION NO. : 15/582212  
DATED : December 24, 2019  
INVENTOR(S) : Conor Leahy et al.

Page 1 of 1

It is certified that error appears in the above-identified patent and that said Letters Patent is hereby corrected as shown below:

In the Specification

In Column 1, Line 31, delete "Abramoff," and insert -- Abràmoff, --, therefor.

In Column 6, Lines 36-37, delete "opthalmoscope," and insert -- ophthalmoscope, --, therefor.

In Column 7, Lines 22-23, delete "opthalmoscope," and insert -- ophthalmoscope, --, therefor.

In Column 7, Line 58, after "images" insert -- . --.

Signed and Sealed this
Seventeenth Day of March, 2020

Andrei Iancu
*Director of the United States Patent and Trademark Office*